(12) United States Patent
Lehner

(10) Patent No.: US 6,258,797 B1
(45) Date of Patent: Jul. 10, 2001

(54) COMBATING INFECTION IN DELIVERY SYSTEMS

(75) Inventor: Joachim Hermann Lehner, Dortmund (DE)

(73) Assignee: Ed. Geistlich Soehne AG fuer Chemische Industrie (CH)

( * ) Notice: Subject to any disclaimer, the term of this patent is extended or adjusted under 35 U.S.C. 154(b) by 0 days.

(21) Appl. No.: 09/331,366

(22) PCT Filed: Dec. 23, 1997

(86) PCT No.: PCT/GB97/03524

§ 371 Date: Jun. 21, 1999

§ 102(e) Date: Jun. 21, 1999

(87) PCT Pub. No.: WO98/28027

PCT Pub. Date: Jul. 2, 1998

(30) Foreign Application Priority Data

Dec. 23, 1996 (GB) .................................................. 9626795

(51) Int. Cl.[7] ........................... A61K 31/54; A01N 43/04
(52) U.S. Cl. ............................................ 514/56; 514/222.5
(58) Field of Search .................................. 514/222.5, 56

(56) References Cited

U.S. PATENT DOCUMENTS

| 5,077,281 | 12/1991 | Reinmüller | 514/56 |
|---|---|---|---|
| 5,167,960 | 12/1992 | Ito . | |

FOREIGN PATENT DOCUMENTS

| 196 06 897 | 8/1997 | (DE) . |
|---|---|---|
| 98/28027 | 7/1998 | (WO) . |
| 99/06114 | 2/1999 | (WO) . |
| 00/01391 | 1/2000 | (WO) . |

OTHER PUBLICATIONS

Messing et al, JPEN, vol. 12, pp. 185–189 (abstract), Mar. 1988.*

Cowan, J. Intraven Nurs., pp. 283–287(abstract), Sep. 1992.*

Gaillaer et al, JPEN, vol. 14, pp. 593–597(abstract), Nov. 1990.*

Elian et al, Arch. Fr. Pediatr., vol. 49, pp. 357–360(abstract), Apr. 1992.*

Bregenzer, Infect. Control Hosp. Epidemiol., vol. 17, p. 772(title), Mar. 1988.*

Jacobi, C.A. et al., "Intraperitoneal Instillation of Taurolidine and Heparin for the Prevention of Intraperitoneal Tumor Growth and Trocar Metastases in Laparoscopic Surgery in a Rat Model," *Langenbecks Arch Chir* (*1997*), vol. 382, No. 4, Suppl. 1, Jul. 25, 1997 pp. S31–S36.

Sodemann, K. et al, "Two Years' Experience with Dialock and CLS™ (A New Antimicrobial Lock Solution)", *Blood Purif*, vol. 19, pp. 251–254, 2001.

Reinmüller, J., "The Effect of Taurolidine on Physiological and Pathological Blood Coagulation and Implications for its Use", Zentralblatt für Chifurgie 1999, Suppl 4:13–18 (translation) (13 pp.).

British Pharmacopoeia 1998, vol. 2, Appendix XVIII, pp. A266–A267.

M. Mughal et al., "Infected Feeding Lines", Care of the Critically Ill, vol. 6, No. 6, 1990, pp. 228–231.

D.A. Johnston et al., "Taurolin for the Prevention of Parenteral Nutrition Related Infection: Antimicrobial Activity and Long–Term Use", Clinical Nutrition, vol. 12, No. 6, 1993, pp. 365–368.

J. I. Blenkharn, "The Antimicrobial Activity of Taurolin—A Possible Additive for Parenteral Nutrition Solutions", Clinical Nutrition, vol. 6, No. 1, 1987, pp. 35–38.

* cited by examiner

*Primary Examiner*—James H. Reamer

(57) ABSTRACT

The use of taurolidine or taurultam in a method of combatting infection or sepsis in delivery systems is disclosed. In the method, taurolidine or taurultam solutions are used as a temporary seal or flush to prevent or reduce sepsis in delivery systems, such as port systems and/or catheters by which liquids are delivered into a patient.

24 Claims, No Drawings

COMBATING INFECTION IN DELIVERY SYSTEMS

This invention relates to a method for preventing and combating infection or sepsis in or caused by the use of delivery systems. More particularly it relates to a method for preventing bacterial colonisation in delivery systems which involve the use of catheters and/or reservoirs of liquid for infusions and the resultant sepsis in vivo. In particular it includes a method for reducing or substantially eliminating infection or sepsis in a subcutaneously-implanted access port for drug delivery either by arterial or venous access or peridural administration.

Delivery systems are widely used in medicine as a means for introducing liquid material which might include medicaments, nutrition, or other active agents to a particular locus in a patient. Such systems frequently involve the use of catheters which, for many applications, are surgically or intravenously located and stitched into place for long-term administration of the desired material. Typical systems include central catheters such as may be used for total parenteral nutrition (TPN) used in e.g. short bowel syndrome (for the duration of life), with the risk of sepsis or endocarditis, as well as catheters and drains which are involved in peritoneal dialysis for those with terminal kidney failure, which, if infected, can lead to peritonitis with serious consequences.

One type of delivery system used for some years in the treatment of conditions in humans comprises a reservoir or chamber of small volume subcutaneously-implanted under the fascia having direct access via a catheter to the cardiovascular system. Such systems are known as port systems.

Such systems are often used in the treatment of malignant conditions. The treatment of malignant conditions in humans is becoming increasing sophisticated and the success rate is rising. Oncology has developed to the stage where particular medicaments or combinations of medicaments, e.g. combinations of cytostatics and metastasis inhibitors, in certain doses either as short or long term infusions or bolus injections can be successfully used to target particular types of malignancy and researchers have sought to develop ways by which regimes of chemotherapeutic medication, some of which can be highly toxic, can be administered to a patient at suitable dosage levels over a period of time. The use of i.v. infusion solutions and/or injections of anti-neoplastic agents can damage veins or cause severe complications such as spasm, paravasal necrosis, (thrombo)phlebitis and sepsis.

One type of reservoir includes a penetrable self-sealing membrane and can be filled or topped-up daily in vivo using a specially-designed syringe and needle. Such a reservoir allows slow continuous discharge of medication over a period of time at a dosage level that can be much more closely maintained and regulated then is the case with other forms of oral or parental administration. Because of the reduction in damage to the veins and discomfort of the patient, the technique clearly has a future but a complication which frequently occurs with serious results is that of infection and sepsis.

The reservoir and delivery system itself in this embodiment is usually implanted under local anaesthesia—below the collar bone in a small pocket created surgically on the fascia of the pectoral muscle is one site that has been used. Whilst all the normal precautions to prevent infection can be taken during implantation, it is in recharging of the device that infection and sepsis is most likely to occur. The system is recharged using the syringe and needle which is passed through the skin and through the self-sealing but penetrable wall of the device. It is difficult to remove all bacteria on the skin prior to recharging and it is inevitable during recharge that some bacteria, for example nosocomial pathogens, and especially resistant pathogens e.g. MRSA or VRE, will be introduced into the system however meticulous the disinfection of the entrance point. Given that therapy is intended to be long-term and that such delivery systems are capable of being recharged up to 2,000 times, there is plenty of opportunity and time for bacterial or fungal infection to take seat and develop into an extremely serious condition. The most common infections are Staphylococcal, such as from multi-resistant *Staphylococcus aureus* (90% penicillin-resistant and methicillin and oxacillin resistant) (MRSA) or from vancomycin-resistant Enterococci (VRE) though other causative organisms such as Streptococci, and rare fungi such as Pseudomonas have also been reported. *Staphylococcus epidermidis* is probably the most frequently reported causative organism.

This situation is exacerbated by the nature of the drug treatment itself. Despite the advances that have been made, oncological chemotherapy still involves treating a patient with materials that are cytotoxic and long-term treatment of this type inevitably weakens the patient's immune system. Anti-neoplastic chemotherapy and radiotherapy lead to immunosuppression in patients. Immunosuppression in patients with malignant tumours leads to reduction of neutrophile granulocytes and neutropenia. Thus, at the same time as an infection may be building up in a patient, his immune system is less capable of dealing with it. The success of anti-neoplastic treatment therefore depends also on the prophylaxis of nosocomial infections in these high-risk patients. Similar considerations apply to the use of such devices in administering medication for the treatment of AIDS.

Similar considerations can apply to other port systems. Other port systems are known for implantation in the arm, known as a peripheral venoid port catheter, for implantation in the peritoneum, for implantation in the hepatic artery and for spinal or epidural implantation.

It is estimated that such ports or catheter-based delivery systems give rise to infections in up to about 8% of cases. The frequency rate and fatality of sepsis does depend on the catheter site, and some of the risk can be reduced by suitable care of the entrance point. However, the consequences of sepsis are clearly dangerous and costly. Removal or replacement of the delivery system may well have to be carried out operatively, necessitating a further stay in hospital for the patient and further expense. The danger of general systemic infection is real and infection in the delivery system is difficult to treat with systemic antibiotics due to the minimal contact time they allow which is insufficient to combat the colonies of multi-resistant pathogens. In addition to this the possible intensive care costs are substantial. The treatment of a patient with severe sepsis can lead to problems such as ARDS (Adult Respiratory Distress Syndrome) necessitating polypragmasy and polypharmacy. The treatment of nosocomial pneumonia or endocarditis are particularly difficult.

Heart problems in particular can also be caused. If a cava catheter through which delivery of the medicament takes place is intubated into one of the veins returning to the heart, for example the cephalic or subclavian vein, the femoral vein, one of the jugular veins or the basilic vein near the elbow, it is guided using X-ray during implantation so that the catheter tip is close to the point of entry of the vena cava into the heart. The heart is accordingly often one of the first organs likely to become colonised by bacteria, fungi or viruses and the feared endocarditis septica has been frequently reported. Other complications include vascular lesions, thrombosis, embolism or phlebitis.

Because the infection has its seat of colonised bacteria within the delivery system, this will not be removed simply by treating the patient systemically with antibiotics. Furthermore, attempts have been made to try and apply antibiotics to the delivery system itself, but this gives rise to difficulties because of the development of resistance problems and because of toxic reactions in the bloodstream which arise when the antibiotic is flushed out of the delivery system with isotonic salt solution. This can result in a toxic allergic bolus-type injection of antibiotics which, in severe cases, can result in anaphylactic shock.

In addition, apart from toxicity problems, a further problem once the delivery system is infected is the release by bacteria of bacterial toxins which result in deposit of a fibrin or collagen net on the internal surface of the delivery system. The net can act as support for the growth of residual resistant and untreatable bacteria leading to superinfection and colonisation by resistant pathogens. Fungi and viruses can also be present. Once this happens, the entire delivery system has to be removed immediately and replaced surgically elsewhere under anaesthetic.

Neither can antiseptics be used to rinse or seal the delivery system because they precipitate a toxic reaction when they are ultimately flushed into the bloodstream. Since anything used to try to remove infection from the delivery system ultimately ends up passing intravenously into the body, the toxicity of general antiseptics completely rules them out of consideration.

We have now found that substantial advantages in the prevention and/or treatment of infection under these circumstances can be obtained if the delivery system is filled, flushed out or sealed when not in use with solutions containing the antibacterial compounds taurultam or taurolidine. These compounds are the only compounds which until now have worked satisfactorily.

These compounds are particularly effective in combating not only infecting bacteria but also in preventing the release of bacterial toxins and as well as inactivating any that may be present. The release of cytokines which activate the coagulation and fibrinolytic systems would be prevented. These compounds are methylol transfer agents and exert their antibacterial activity by reacting with the bacterial cell wall components and forming covalent bonds. Despite, therefore, the possibility of quite lengthy residence time in the delivery system, they have been found not to cause any build-up of resistance. This is not the case with other conventional antibiotics.

In the context of the present situation, this fact that these compounds avoid the development of any resistance is a huge advantage. A solution of taurultam or taurolidine can be used to seal the delivery system between each administration of desired liquid material, such as chemotherapeutic agent or nutrient, or after withdrawal of any blood sample from the reservoir. Should there be any period of time when it is desired not to use the delivery system for administration of chemotherapeutic or other active or nutritional agent, such as is often the case during the cyclical delivery of chemotherapeutic agents or during total parenteral nutrition, the delivery system can be filled with a taurolidine or taurultam solution to act as an antimicrobial seal. Relatively small volumes (of the order of a few milliliters, e.g. approximately 3 ml) of taurolidine or taurultam are required for this. A contact time of about one hour is desirably a minimum, though the seal can be retained for up to twelve hours or more. All of these activities can be carried out without any development of resistance or build up of bacterial toxins such as LPS and exotoxins by resident bacteria. Taurolidine solutions are well tolerated i.v., as there is no toxicity and no side effects have been observed.

Accordingly, viewed from one aspect, we provide the use of taurolidine or taurultam solutions as a temporary seal to prevent or reduce infection and sepsis associated with the use of a delivery system. This is of particular application to the use of catheters.

Viewed from another aspect, the invention comprises the use of taurolidine or taurultam solutions to reduce or prevent infections associated with the use of subcutaneously-implanted delivery systems. These are of particular application to systems which deliver medication from a reservoir via catheter into the cardiovascular system, such as might be used during chemotherapy.

A preferred solution will contain from 0.5 to 3% by weight of taurolidine, or from 1 to 7.5% by weight taurultam, advantageously 3 to 5%, depending on the solubility of the compound. Solutions containing from 1.0 to 2.0% taurolidine are preferred.

The solutions will generally be made up in sterile pyrogen-free water and may also contain, for example, inorganic or other salts or other components to render them isotonic. Parenterally acceptable polyols may, for example, also be present since these have been observed to increase the overall intravenous tolerance of taurolidine. Suitable polyols include carbohydrates, e.g. hexoses such as glucose and fructose (or mixtures of these such as invert sugar), pentoses such as xylose or polysaccharides such as dextran or hydrolysed starch; glycerol and sugar alcohols such as sorbitol, mannitol or xylitol.

The concentration of the polyol can usefully be in the range 3–40% by weight. In the case of glucose, the concentration may be in the range 10–30% by weight, preferably 20%.

The solutions may also contain polyvinylpyrrolidone (PVP). This may be incorporated into the solutions at a concentration of, e.g. from 4 to 7% by weight. A solution containing 5% PVP is preferred. This assists in solubilising the active substance and contributes also to the oncotic pressure of the solution. The molecular weight of the PVP should not be greater than 30,000 and is preferably less than 10,000, for example between 7000 and 9000. Kollidone 17 as sold by BASF is relatively quickly resorbed and excreted renally.

The use of taurolidine or taurultam has not been found to give rise to any adverse side-reactions and there appear to be no compatibility problems with the plastic materials of which a delivery reservoir or catheter can be made. Indeed, the use of taurolidine appears to have the further advantage that it can reduce the adhesiveness of fibrin deposits within a plastic delivery system, thus leading to a lower incidence of residual bacteria and infections.

Typical procedures, which should not be considered as limiting, are as follows:

1.) A patient has a Port delivery system comprising a polyurethane chamber of approx. 0.5 cm$^3$ volume mounted on a small titanium plate implanted in a small pocket in the pectoral muscle. The tip of a catheter of approx 0.3 mm diameter leading from it has been intubated into one of the major veins and lies close to the point of entry of the vena cava into the right atrium of the heart. After implantation the chamber was flushed through with 2 ml of a sterile 0.9% by weight sodium chloride solution containing 800 I.E. heparin.

The chamber is then filled with approximately 3 ml of a 2% by weight Taurolin® (taurolidine) solution (injected into the chamber by special syringe) and the device sealed for up to 12 hours or until whenever chemotherapeutic administration is due.

Prior to introducing a cancer chemotherapeutic agent, for example, the taurolidine solution is rinsed into the bloodstream using saline. Cancer chemotherapeutic agent as desired is then injected into the chamber and is taken into the body over a period of time. Examples of possible such agents include the alkylating agents, such as numistin hydrochloride and cyclophosphamide; antimetabolites such as fluorouracil, cytarabine and methotrexate; anti-tumour antibiotics such as bleomycin sulphate, daunorubicin hydrochloride and idarubicin hydrochloride; alkaloids such as lincristine sulphate and cisplatins such as carboplatin. These agents are administered via the port system in different formulations for several short-term and long-term infusions or for bolus injections.

After each treatment with medication, or after use of the chamber to withdraw a sample of venous blood, the delivery system is rinsed meticulously with 10 ml of a sterile 0.9% sodium chloride solution. 2 ml of a 2% Taurolin® solution are then introduced into the chamber and the needle removed. The port system is then effectively sealed against microbial infection. After being rinsed with saline, further medication may then be introduced when desired and the cycle repeated.

2.) A patient undergoing total parenteral nutrition is fitted with a central catheter by known techniques. Nutrition is delivered overnight whilst the patient is asleep but during the day the catheter is sealed with approximately 3 ml of 2% taurolidine solution. Such an amount and concentration is effective to prevent catheter sepsis, has no side effects when it passes into the body when nutrition recommences possibly several hours later, and has clear advantages over the alternative procedure which involves using large volumes of antibacterial agents mixed with and administered along with the nutrient mix itself.

What is claimed is:

1. The use of a solution of taurolidine or taurultam as a temporary seal to prevent or reduce infection and sepsis in liquid delivery systems.

2. Use as claimed in claim 1 wherein the delivery system involves use of a catheter.

3. Use as claimed in claim 1 wherein the delivery system is a subcutaneously implanted delivery system, or port system.

4. Use as claimed in claim 1 wherein the solution contains from 0.5 to 3% by weight of taurolidine or from 1 to 7.5% by weight of taurultam.

5. Use as claimed in claim 1 wherein the solution contains about 3 ml taurolidine or taurultam.

6. A method of preventing or reducing infection and/or sepsis in a liquid delivery system which comprises temporarily sealing said system with a solution of taurolidine or taurultam.

7. The method as claimed in claim 6 wherein said step of temporarily sealing said system is performed after administration of a desired liquid material.

8. The method as claimed in claim 6 wherein said step of temporarily sealing said system is performed after removal of a blood sample.

9. The method as claimed in claim 6 wherein said step of temporarily sealing said system is performed whenever it is desired not to use said system for administration of a desired liquid material or removal of a sample.

10. The method as claimed in claim 6 wherein said step of temporarily sealing said system includes filling said system with a solution of taurolidine or taurultam to act as an antimicrobial seal.

11. The method as claimed in claim 10 further comprising the step of retaining said seal for at least one hour.

12. A method of preventing or reducing infection and sepsis in a liquid delivery system which comprises a step of temporarily sealing said system with a solution including taurolidine or taurultam, wherein said step of temporarily sealing said system includes filling said system with the solution to act as an antimicrobial seal, and wherein said system includes a subcutaneously-implanted port system and said filling step includes the steps of injecting the solution into the port system using a syringe and removing the syringe when the system is sealed.

13. The method as claimed in claim 12 wherein the solution is injected into the port system through a wall of the port system.

14. A method of preventing or reducing infection and sepsis in a liquid delivery system having a liquid-containing surface, the liquid delivery system being connected to a patient for delivery of a liquid to said patient, the method comprising contacting said surface with a first solution containing an anticoagulant agent, and thereafter contacting said surface with a second solution containing at least one of taurolidine and taurultam.

15. The method of claim 14 wherein the second solution is contacted with said surface for at least about 1 hour.

16. The method of claim 15 wherein the second solution is sealed in said delivery system for a period of up to about 12 hours.

17. The method of claim 16 wherein the second solution which is sealed in said delivery system is replaced at least about daily.

18. The method of claim 14 wherein, when contacting said surface with the first solution containing an anticoagulant agent, said surface is flushed with said anticoagulant-containing solution.

19. The method of claim 18 wherein the second solution is contacted with said surface for at least about 1 hour.

20. The method of claim 19 wherein the second solution is sealed in said delivery system for a period of up to about 12 hours.

21. The method of claim 20 wherein the second solution which is sealed in said delivery system is replaced at least about daily.

22. The method of claim 14 wherein the second solution contains at least one of about 0.5 to about 3% by weight of taurolidine and about 1 to about 7.5% by weight of taurultum.

23. The method of claim 14 wherein said anticoagulant agent is heparin.

24. The method of claim 23 wherein the first solution includes about 0.9% by weight sodium chloride and about 800 I.E. heparin.

* * * * *

US006258797C1

(12) EX PARTE REEXAMINATION CERTIFICATE (5135th)
United States Patent
Lehner

(10) Number: US 6,258,797 C1
(45) Certificate Issued: Jul. 5, 2005

(54) COMBATING INFECTION IN DELIVERY SYSTEMS

(75) Inventor: Joachim Hermann Lehner, Dortmund (DE)

(73) Assignee: Ed Geistlich Sohne AG fur Chemische Industrie, Wolhusen (CH)

Reexamination Request:
No. 90/006,195, Jan. 22, 2002

Reexamination Certificate for:
Patent No.: 6,258,797
Issued: Jul. 10, 2001
Appl. No.: 09/331,366
Filed: Jun. 21, 1999

(22) PCT Filed: Dec. 23, 1997

(86) PCT No.: PCT/GB97/03524
§ 371 (c)(1),
(2), (4) Date: Jun. 21, 1999

(87) PCT Pub. No.: WO98/28027
PCT Pub. Date: Jul. 2, 1998

(30) Foreign Application Priority Data

Dec. 23, 1996 (GB) .............................................. 9626795

(51) Int. Cl.[7] ...................... A61K 31/727; A01N 43/04
(52) U.S. Cl. ..................................... 514/56; 514/222.5
(58) Field of Search ................................ 514/56, 222.5

(56) References Cited

U.S. PATENT DOCUMENTS

| | | | |
|---|---|---|---|
| 3,423,408 A | | 1/1969 | Pfirmann |
| 4,587,268 A | | 5/1986 | Pfirmann |
| 4,960,415 A | * | 10/1990 | Reinmuller .................. 604/890 |
| 5,077,281 A | | 12/1991 | Reinmuller |
| 5,210,083 A | * | 5/1993 | Pfirmann .................. 514/222.5 |
| 5,263,930 A | * | 11/1993 | Ensminger .................... 604/93 |
| 5,352,204 A | | 10/1994 | Ensminger |
| 5,433,705 A | * | 7/1995 | Giebel et al. .................. 604/82 |
| 6,146,363 A | | 11/2000 | Giebel et al. |
| 6,174,537 B1 | | 1/2001 | Khan |

OTHER PUBLICATIONS

Mughal Br. J. Surg. (1989) vol. 76 (1), pp. 15–21.*
Krzywda et al. Infection Control and Hospital Epinemiology (1995), vol. 16 (10), pp. 596–598.*
Browne et al. Journal of Applied Bacteriology (1976), vol. 41, pp. 363–368.*
Jurewitsch et al. J. Parent. & Enteral Nutrition (1998), vol. 22 (4), pp. 242–244.*
Budvari et al. (Eds), The Merck Index (12th Ed.), (1996), pp. 696, 1553, 1686, and paragraph 9243.*
Palm et al. Laboratory Animals (1991), vol. 25, pp. 142–152.*
Mughal et al. Care of the Critically III (1991), vol. 6 (6), pp. 228–232.*
Schwartz et al. J. Clinical Oncol. (1990), vol. 8 (9), pp. 1591–1597.*

M. Mughal, "Complications of intravenous feeding catheters," Br. J. Surg. (Jan. 1989) 76(1):15–21.
Reeves et al., "Experimental Studies with an Antibacterial Substance, Taurolin," Proceedings of the 8th International Congress of Chemotherapy 1974; 2:583.
Benoit et al., "Intraluminal Antibiotic Treatment of Central Venous Catheter Infections in Patients Receiving Parenteral Nutrition At Home," Clinical Infectious Diseases (1995) 21:1286–88.
Messing et al., "Antibiotic–Lock Technique: A New Approach to Optimal Therapy for Catheter–Related Sepsis in Home–Parenteral Nutrition Patients," J. Paren. & Enter. Nutrit. (1988) 12(2):185–89.
Mughal et al., "Infected Feeding Lines," Care Of The Critically ill (Nov./Dec. 1991) 6(6):228–32.
Elian et al., "Etude de la cinetique serique de la vancomycine au decours de la technique de 'blocage in situ'," Arch Fr. Pediatr.(1992) 49:357–60 (Translation Provided).
Cowan C E, "Antibiotic Lock Technique," J. Intravenous Nurs. (Sep./Oct. 1992) 15(5):283–287.
Palm Ue, Boemke W, Reinhardt H W, "Verhinderung katheterbedingter Infektionen, eine experimentelle Langzeituntersuchung," Der Anesthesist 1989 38 (Supp. 1):129 (Translation Provided).
Palm Ue, Boemke W, Bayerl D, Schnoy N, Juhr N C, and Reinhardt W, "Prevention of catheter–related infections by a new, catheter–restricted antibiotic filling technique," Laboratory Animals (1991) 25:142–52.
Gaudry et al., "Est–il possible de conserver un catheter infecte?," Nephrologie (1994) 15:171–72 (Translation Provided).
Johnson et al., "Preliminary Results Treating Persistent Central Venous Catheter Infections With The Antibiotic Lock Technique In Pediatric Patients," Pediatric Infectious Disease Journal (1994) 13(10) 930–31.
Yazbeck et al., "The Antibiotic Lock Technique Used In An Infected Catheter: Preventive Therapy," Proceedings of the International Multidisciplinary Symposium, Angioaccess for Hemodialysis, Jun. 3–5, 1996, 189–90.
Gaillard et al., "Conventional and Nonconventional Modes of Vancomycin Administration to Decontaminate the Internal Surface of Catheters Colonized with Coagulase–Negative Staphylococci," J. Parenter. & Enter. Nutrit. (1990) 14(6):593–97.
Krzywda et al., "Treatment of Hickman Catheter Sepsis Using Antibiotic Lock Technique," Infection Control and Hospital Epidemiology (Oct. 1995) 16(10): 596–98.
Bregenzer T and Widmer A F, "Bloodstream Infection From a Port–A–Cath: Successful Treatment with the Antibiotic Lock Technique," Infection Control & Hosp. Epidemiology (1996) 17:772.

(Continued)

Primary Examiner—Samuel Barts

(57) ABSTRACT

The use of taurolidine or taurultam in a method of combating infection or sepsis in delivery systems is disclosed. In the method, taurolidine or taurultam solutions are used as a temporary seal or flush to prevent or reduce sepsis in delivery systems, such as port systems and/or catheters by which liquids are delivered into a patient.

OTHER PUBLICATIONS

Henrickson et al., "Modification of Central Venous Catheter Flush Solution Improves In Vitro Antimicrobial Activity," *J. Infect. Diseases* (1992) 166:944–46.

Root et al., "Inhibitory Effect of Disodium EDTA upon the Growth of *Staphyloccoccus epidermis* In Vitro: Relation to Infection Prophylaxis of Hickman Catheters," *Antimicrobial Agents and Chemotherapy* (1988) 32(11):1627–31.

Schwartz et al., "Prevention of Bacteremia Attributed to Luminal Colonization of Tunneled Central Venous Catheters With Vancomycin–Susceptible Organisms," *J. Clinical Oncol.* (1990) 8(9): 1591–97.

Winters et al., "A Trial With a New Peripheral Implanted Vascular Access Device," *Onc. Nurs. For.* (1990) 17(6):891–96, at 893, bottom of Col. 1 to top of Col. 2.

Worthley, "Treatment of Central Venous Silastic Catheter Infections Using Hydrochloric Acid," *Anaesth. Intens. Care*, 1982, 10:314.

Elliott T S J and Curran A, "Effects of heparin and chlorbutol on bacterial colonisation of intravascular cannulae in an in vitro model," *J. Hospital Infection* (1989) 14: 193–200.

Johnston D A, Phillips G, Richards J, and Pennington C, "Antimicrobial activity and long–term use of Taurolin as an additive to parenteral nutrition," *Proceedings Nutrition Soc.* 1993 52:245A (Meeting of Dec. 2/3, 1992).

Johnston D A, Phillips G, Perry M, McAlpine H, Richards J, and Pennington C R, "Taurolin for the Prevention of Parenteral Nutrition Related Infection: Antimicrobial Activity and Long Term Use," *Clinical Nutrition* (1993) 12(6):365–68.

Blenkharn J I, "The Antimicrobial Activity of Taurolin®—A Possible Additive for Parenteral Nutrition Solutions," *Clinical Nutrition* (1987) 6:35–38.

Blenkharn J I, "Prevention of Septic Complications Associated with TPN," *J. Paren. & Enter. Nutrition* (1986) 10(4):436–37.

Knight et al., "NMR Studies and GC Analysis of the Antibacterial Agent Taurolidine," *J. Pharmaceutical Sciences* (1983) 72(6):705–07.

Myers et al, "The Relationship between Structure and Activity of Taurolin," *J. Applied Bacteriology* (1980) 48:89–96.

Browne et al., "Taurolin, a New Chemotherapeutic Agent," *Journal of Applied Bacteriology* 1976, 41:363–68.

Brearly et al., "The Rate of Antimicrobial Action Of Nozythiolin and Taurolin," *J. Hosp. Infection* (1980) 1:201–09.

Browne et al., "The In Vitro and In Vivo Activity of Taurolin Against Anaerobic Pathogenic Organisms," *Surgery, Gynecology & Obstetrics* (Dec. 1977) 145:842–46.

Traub et al., "Taurolidine: in vitro Activity against Multiple–Antibiotic Resistant, Nosocomially Significant Clinical Isolates of *Staphylococcus aureus, Enterococcus faecium*, and Diverse Enterobacteriaceae," *Chemotherapy* (1993) 39:322–30.

*Stedman's Medical Dictionary* ($26^{th}$ Ed.) (Williams & Wilkins 1995), pp. 1587, 1843.

Budvari, et al. (Eds.), "The Merck Index ($12^{th}$ Ed.)," Merck & Co., Inc. (New Jersey 1996) pp. 696, 1553, 1686, section 9243 (taurolidine).

C. R. Bard, Inc., "Care of Groshong Catheters" (1994).

Raad et al., "Minocycline and Ethylenediaminetetraacetate for the Prevention of Recurrent Vascular Catheter Infections," *Clinical Infectious Diseases* 1997 25:149–51.

Oguz et al., "Effect of taurolidine on the normal eyelid and conjunctival flora," *Current Eye Research* (2000) 21(5):851–855.

Farber B F, Kaplan M H, & Clogston A G, "*Staphylococcus epidermis* Extracted Slime Inhibits the Antimicrobial Action of Glycopetide Antibiotics," *J. Infectious Diseases* (1990) 161:37–40.

Jurewitsch B, Lee T, Park J, & Jeejeebhoy K, "Taurolidine 2% as an Antimicrobial Lock Solution for Prevention of Recurrent Catheter–Related Bloodstream Infections," *J. Parent. & Enteral Nutrition* (1998) 22(4):242–244.

* cited by examiner

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1–24 are cancelled.

New claims 25–42 are added and determined to be patentable.

25. *A method of preventing or reducing infection and sepsis in a liquid delivery system, comprising:*
   a) *passing a desired liquid material through the liquid delivery system, wherein said system comprises a port or catheter implanted in a patient;*
   b) *after step a), filling the liquid delivery system with a water-based solution comprising taurolidine or taurultam, so as to contact portions of the liquid delivery system which contacted said desired liquid material during said passing;*
   c) *forming a temporary seal in said liquid delivery system with said solution contained within said liquid delivery system so as to prevent or reduce infection and sepsis in said liquid delivery system;*
   d) *thereafter removing said temporary seal and repeating steps a), b) and c).*

26. *The method of claim 25 wherein, in step b), the liquid delivery system is filled with said water-based solution using a syringe.*

27. *The method of claim 25 wherein said solution is sealed in said liquid delivery system for at least for about one hour.*

28. *The method of claim 25 wherein said solution is sealed in said liquid delivery system for up to 12 hours.*

29. *The method of claim 25 wherein said water-based solution comprises taurolidine at a concentration of about 0.5–3% by weight said taurolidine.*

30. *The method of claim 25 wherein said water-based solution comprises taurultam at a concentration of about 1-7.5% by weight taurultam.*

31. *The method of claim 25 wherein, in step c), said liquid delivery sytem is sealed with up to about 3 ml of said water-based solution contained within said liquid delivery system.*

32. *The method of claim 25, wherein in step d), prior to repeating steps a), b) and c), said liquid delivery system is rinsed using saline.*

33. *The method of claim 25 wherein said passing in step a) is for administration of said desired liquid material to said patient.*

34. *The method of claim 25 wherein said passing in step a) is for removal of a sample of said desired liquid material from said patient.*

35. *The method of claim 34 wherein said sample is a blood sample of said patient.*

36. *The method of claim 25 wherein said water-based solution further comprises a parenterally acceptable polyol.*

37. *The method of claim 36 wherein said polyol is at concentration in a range of about 3–40% by weight.*

38. *A method of claim 25 wherein said water-based solution further comprises PVP.*

39. *The method of claim 38 wherein said PVP is at a concentration in said solution of about 4–7% by weight.*

40. *The method of claim 39 wherein said PVP as a molecular weight not greater than 30,000.*

41. *The method of claim 40 wherein said PVP has a molecular weight less than 10,000.*

42. *The method of claim 41 wherein said PVP has a molecular weight between 7,000 and 9,000.*

* * * * *